United States Patent [19]
Paul et al.

[11] Patent Number: 6,019,882
[45] Date of Patent: Feb. 1, 2000

[54] ELECTROKINETIC HIGH PRESSURE HYDRAULIC SYSTEM

[75] Inventors: Phillip H. Paul, Livermore; David J. Rakestraw, Fremont, both of Calif.

[73] Assignee: Sandia Corporation, Albuquerque, N. Mex.

[21] Appl. No.: 09/057,017

[22] Filed: Apr. 7, 1998

Related U.S. Application Data

[63] Continuation-in-part of application No. 08/882,725, Jun. 25, 1997.
[51] Int. Cl.$^7$ .............................. C12Q 1/68; B01J 19/00; G01N 33/48
[52] U.S. Cl. .......................... 204/450; 204/600; 204/647; 204/648
[58] Field of Search .................................... 204/450, 600, 204/647, 648

[56] References Cited

U.S. PATENT DOCUMENTS 5,593,838  1/1997  Zanzucchi et al. ..................... 204/450

OTHER PUBLICATIONS

Pretorius et al., "A New Concept for High–Speed Liquid Chromatography." Journal of Chromatography pp. 23–30, 1974.

Primary Examiner—Arun S. Phasge
Attorney, Agent, or Firm—Donald A. Nissen

[57] ABSTRACT

A compact high pressure hydraulic pump having no moving mechanical parts for converting electric potential to hydraulic force. The electrokinetic pump, which can generate hydraulic pressures greater than 2500 psi, can be employed to compress a fluid, either liquid or gas, and manipulate fluid flow. The pump is particularly useful for capillary-base systems. By combining the electrokinetic pump with a housing having chambers separated by a flexible member, fluid flow, including high pressure fluids, is controlled by the application of an electric potential, that can vary with time.

3 Claims, 3 Drawing Sheets

ELECTROKINETIC HIGH PRESSURE HYDRAULIC SYSTEM

CROSS-REFERENCE TO RELATED APPLICATIONS

This application is a continuation-in-part of prior co-pending U.S. patent application Ser. No. 08/882,725 filed Jun. 25, 1997.

STATEMENT OF GOVERNMENT INTEREST

This invention was made with Government support under contract no. DE-AC04-94AL85000 awarded by the U. S. Department of Energy to Sandia Corporation. The Government has certain rights in the invention.

BACKGROUND OF THE INVENTION

This invention pertains generally to a method for producing high pressures that requires no moving mechanical parts and particularly to the use of electro-osmotic flow to produce a high pressure system for compressing and manipulating fluids in packed microchannels, in general, and capillaries, in particular.

The phenomenon of electro-osmosis, in which the application of an electric potential to an electrolyte in contact with a dielectric surface produces a net force on a fluid and thus a net flow of fluid, has been known since Reuss in 1809. The physics and mathematics defining it and its associated phenomenon streaming potential, both part of a larger class of electrochemical phenomena, namely electrokinetic effects, have been extensively explored, *Introduction to Electrochemistry*, S. Glasstone, 1942, pp. 521–529 and R. P. Rastogi, "Irreversible Thermodynamics of Electro-osmotic Flow", *J. Sci. and Industrial Res.*, 28, 284, 1969. In like manner, electrophoresis, the movement of charged particles through a stationary medium under the influence of an electric field, has been extensively studied and employed in the separation and purification arts.

The use of electro-osmotic flow has been wide spread and has found wide ranging applications in chemical analysis. The use of electro-osmostic flow for fluid transport in packed bed capillary chromatography was first documented by Pretorius, et. al., "Electro-osmosis—A New Concept for High-Speed Liquid Chromatography", *J. Chromatography*, 9, 23–30, 1974. Although the possibility of using this phenomenon was recognized two decades ago, the effective use of this method has only recently been demonstrated and has just begun (within the last year) to provide commercial utility.

As set forth hereinabove, although electro-osmosis has been used extensively to move or pump fluids, except for measurements of the streaming potential, there appears to be no recognition that this same phenomenon can be used to generate large pressures, or resistive forces, (in excess of 2500 psi) which can be used to compress or pump fluids and manipulate fluid flow generally in capillary-based systems.

SUMMARY OF THE INVENTION

The present novel invention uses electro-osmotic flow to provide a high pressure hydraulic system, having no moving mechanical parts, for pumping and/or compressing fluids and manipulating fluid flow in packed (i.e., having a porous dielectric material disposed in a fluid passageway) capillary-based systems (Microsystems).

Except for very general references to the fact that pressures generated by electro-osmotic flow were linearly proportional to the applied voltage (cf. Dasgupta and Liu, *Analytical Chemistry*, 1194, 66, 1793 and Theeuwes U.S. Pat. No. 3,923,426 at col. 1 line 23) there appeared to be no recognition in the prior art that electro-osmosis could be used to generate high pressure. Those experimental studies that did explore the relationship between electro-osmosis and pressure, generally studies of streaming potential, were limited to pressures below 1 psi (Rastogi, ibid. and Cooke, *J. Chem. Phys.*, 1995, 23, 2302). Moreover, Rastogi, ibid., 291, has shown that the then recognized linear dependence of electro-osmotic pressure and applied electric potential begins to fail at voltages of about 300 to 400 Volts and pressures above about 0.2 to 0.3 psi and, in fact, pressure begins to approach an asymptote of between 0.3 to 0.4 psi at an applied electric potential on the order of 600 Volts. Thus, prior art did not recognize and, in fact, taught away from being able to achieve pressures above about 1 psi by means of electro-osmosis. It is believed that the cause of the non-equilibrium pressure/applied electric potential effects observed in earlier work may be the result of using capillaries having too large a diameter and/or solutions having too high a conductivity which can cause undesirable heating of the electrolyte to the point where boiling and bubble formation can take place.

Contrary to prior art teachings, the inventors have discovered by both theoretical prediction and by experimental studies that in a capillary-based system electro-osmotic flow can generate pressures as high as 5000 psi and that the relationship between electro-osmotic pressure and applied electric potential is linear up to and including pressures as high as 5000 psi (FIG. 4).

The ability to pressurize a fluid in microsystems by means of an electric potential provides a means for imparting net power to the fluid and by this means to transmit and use this net power to perform work (apply force) on some system. It will be appreciated that the ability to convert the hydraulic action produced by the system disclosed herein to mechanical action and work can encompass exerting hydraulic pressure on a diaphragm or hydraulic drive of a positive displacement fluid motor, or hydraulic flexure of a fluid-filled member, or expansion or contraction of a fluid-filled bellows, or extension or retraction of a fluid-filled piston, or any other means known in the art of converting hydraulic action, power and work to mechanical action, power and work.

The invention comprises at least one capillary channel or microchannel forming a fluid passageway and having a porous dielectric medium disposed therein between one or more spaced electrodes. The porous dielectric medium can comprise small particles, high surface area structures fabricated within the microchannel, or microporous materials. An electric potential can be applied between the electrodes in contact with an electrolyte (i.e., a solution containing ions and generally capable of ionic conduction) contained within the pores of the porous dielectric medium in order to cause the electrolyte to move in the microchannel. The present invention can be characterized by two separate embodiments.

The direction of flow of the electrolyte is determined by both the nature of the electrochemical interaction between the porous dielectric medium and the electrolyte and the polarity of the applied electric potential. Further, the flow rate of the electrolyte induced by these effects is proportional to the magnitude of the applied electric potential.

In one embodiment, the invention is configured such that an electrolyte contained in a porous dielectric medium disposed within a capillary or microchannel can act as a valve; the electrolyte being selectively moveable between a first position opening communication between a fluid inlet and an outlet and a second position closing communication between the fluid inlet and outlet. Opening and closing the valve is provided by applying an electric potential between the spaced electrodes sufficient to cause the electrolyte to move from the first position to the second. The process can be reversed simply by reversing the polarity of the electric potential.

The inventors have further discovered that by applying an electric potential to an electrolyte contained in a porous dielectric disposed within a capillary or microchannel, the system disclosed herein is capable of exerting high pressures (e.g., at least 2500 psi). Thus, in a second embodiment, the invention is configured to compress a fluid, which can be either a liquid or a gas. Here a fluid outlet can be either completely sealed or constricted such that when an electric potential is applied between spaced electrodes, movement of the electrolyte causes the fluid which resides between the electrolyte and the sealed or constricted outlet to be compressed.

The above-described electrokinetic high pressure hydraulic system has several advantageous features. There are no moving mechanical parts and all liquid seals, thus the system is not subject to frictional wear. Since the system is driven electrically and has no moving mechanical parts it can be rapidly turned on and off. By applying periodic electrical potentials, whose periods can be various functions of time, to a plurality of spaced electrodes different timing arrangements such as might be useful for varying compression and valving cycles can be effected. Moreover, the system is capable of remote operation.

BRIEF DESCRIPTION OF THE DRAWINGS

The accompanying drawings, which are incorporated in and form part of the specification, illustrate the present invention and, together with the description, explain the invention. In the drawings like elements are referred to by like numbers.

FIG. 1 illustrates a valve embodiment of the present invention.

DETAILED DESCRIPTION OF THE INVENTION

Figure 1A:
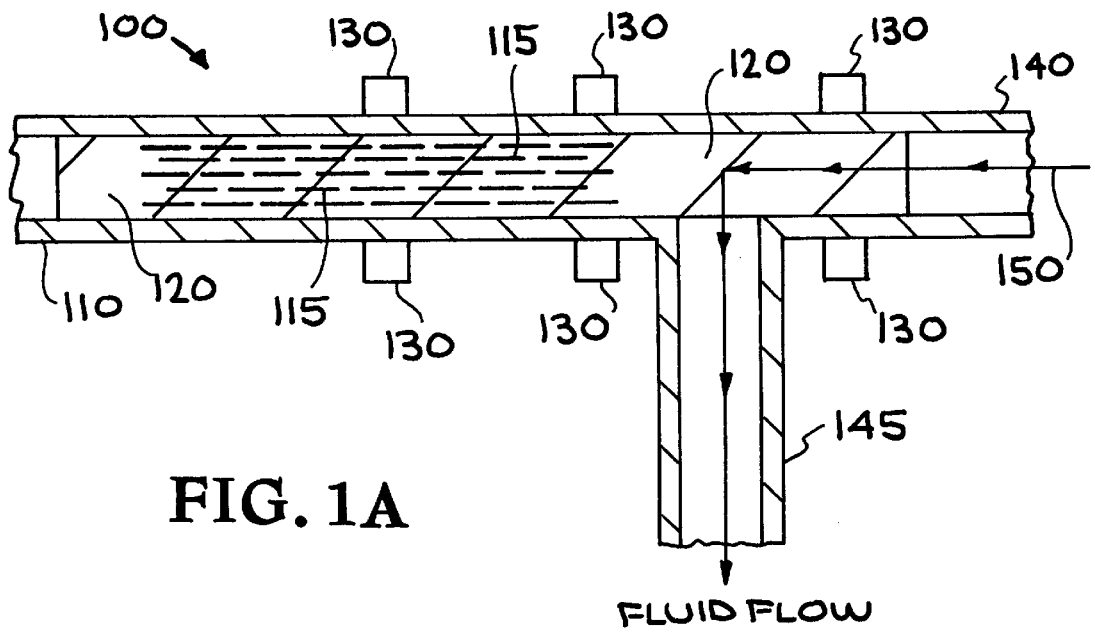
FIG. 1(a) shows the valve in the open position.

The present invention pertains generally to a high pressure hydraulic system and is particularly adapted for use in packed capillary-based systems. Electro-osmotic flow is used to provide a high pressure hydraulic system having no moving mechanical parts for pumping and/or compressing fluids and manipulating fluid flow within capillaries.

For the purpose of describing the invention disclosed herein the term microchannel, as used hereinafter, will refer to a flow channel whose internal dimensions are on the order of tens to hundreds of microns. Generally, these systems are referred to as capillary or capillary-based systems, however, the flow channels contemplated by this invention can have an arbitrary cross-sectional geometry, in addition to the circular cross-section conventionally associated with capillaries, and can be fabricated from any material providing that the material is not an electrical conductor.

It is contemplated that the present invention can be advantageously used in Microsystems (i.e., systems having dimensions on the order of tens to hundreds of microns) for fluid manipulation generally and, in particular, for compression/expansion of gases and high pressure injection of fluids. The present invention can also find advantageous use as a miniature vacuum pump or a miniature hydraulic pump. Moreover, because the present system exhibits only a very small dead volume it can be used for precise handling of gases.

In order for the electro-osmotic forces useful for this invention to be generated it is necessary that a porous dielectric medium be present in at least one of the microchannels. It is known in the art that electro-osmosis is generally attributable to the formation of an electric double layer at the interface between a solid and a liquid containing ions. As a consequence of the formation of the electric double layer, an electrically charged diffuse layer is formed extending from the solid-liquid interface into the bulk of the liquid. While a double layer can be formed anytime a liquid containing ionic species comes into contact with a solid surface, its physical manifestation is most easily observed in capillary systems. Here, under the influence of a tangential electric field the diffuse layer is caused to move and will flow at a constant rate depending upon the equilibrium established between frictional forces developed between the moving liquid and the wall of the capillary and the electro-osmotic force due to the electric forces acting on the excess ionic charge in the diffuse layer. If the liquid, under the influence of electro-osmotic forces, is allowed to accumulate at the outlet end of the capillary an excess hydrostatic pressure can be developed which can eventually counterbalance the electro-osmotic forces.

The inventors have discovered both by theoretical prediction and by physical observation that the pressure differential between the inlet and outlet of the system disclosed herein is proportional to the magnitude of the electric potential applied to one or more pairs of spaced electrodes and that the direction of fluid flow is dependent upon the polarity of the applied electric potential. Thus, the magnitude and direction of fluid flow and pressure and thereby the direction and magnitude of the flow of power, work or force imparted by the fluid is dependent on the polarity and magnitude of the applied electric potential.

Porous dielectric materials useful for this invention can take a number of forms in addition to the more conventional silica structures such as beads or frits. Such structures can be fabricated, by way of example, by lithographic patterning and etching, direct injection molding, sol-gel processes, and high energy lithography combined with electroforming and molding (LIGA) as well as organic polymeric materials.

A valve embodiment of the present invention can be illustrated by reference to FIG. 1(a). Valve 100 comprises a T-shape flow system, wherein microchannel 110 contains a porous dielectric 120, extending past outlet 145 about 1–2 channel diameters, that can include fine particles, preferably silica having a diameter of about 100 nm to 5 μm, or other high surface area features such as might be produced by microfabrication methods known to those skilled in the art, preferably by lithographic etching, and which present a porous matrix having a high surface area for electrolyte solution 115 to flow through. Fluid inlet 140 and outlet 145 in communication with microchannel 110 provide for the flow of a fluid (liquid or gas) 150 therethrough.

Figure 1B:
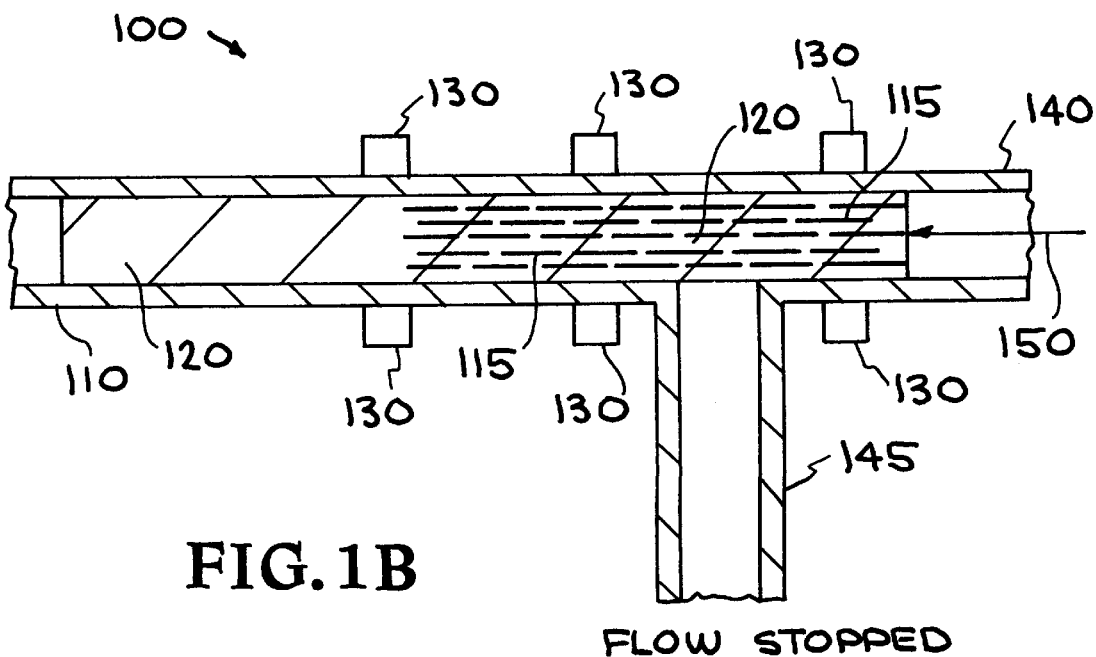
FIG. 1(b) shows the valve in the closed position.

Referring now to FIG. 1(b), in order to close communication between fluid inlet 140 and outlet 145 an electric potential is applied by a power supply (not shown) to spaced electrodes 130 to provide the electro-osmotic force required to move electrolyte 115, to close fluid outlet 145, and prevent fluid 150 from flowing through outlet 145. Valve 100 can be opened by simply shutting off the electric potential applied to spaced electrodes 130. Valve 100 can be caused to operate in the opposite direction by simply reversing the sign of the electric potential applied to spaced electrodes 130.

It is contemplated that the electric potential applied between spaced electrodes 130 can, in addition to the step function form described hereinabove, assume various other forms suitable to the operation of the system described herein such as oscillatory having a varying shape and period.

Figure 5:
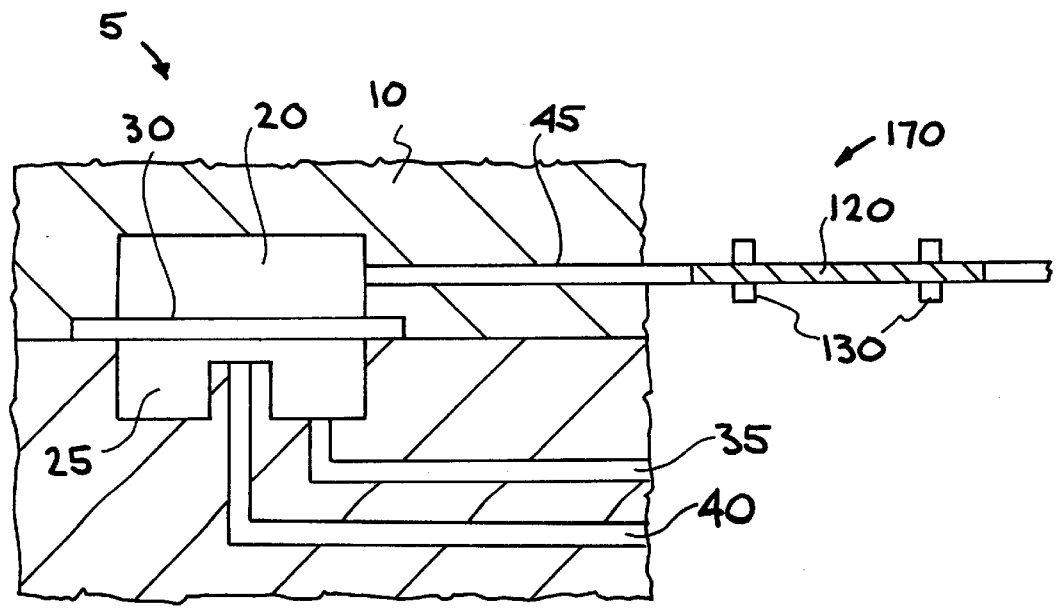
FIG. 5 shows a second valve embodiment.

A second valve embodiment is shown in FIG. 5 that provides for controlling the flow of a fluid that can be either a liquid or a gas. Here, a housing 10 has a cavity formed in its inner surface. The cavity is divided into two chambers 20 and 25 separated by a fluid tight flexible member 30. Flexible member 30 can be made from materials that are compatible with fluids that are contained in chambers 20 and 25 and are flexible by virtue of their composition or mechanical design. A fluid stream enters chamber 25 through fluid inlet line 40 and exits through fluid outlet line 35. The flow of the fluid stream is controlled by applying hydraulic pressure generated by electro-osmotic pump 170 through inlet line 45 to the fluid contained in chamber 20 and in turn on flexible member 30 causing it to deform and thereby close off fluid inlet line 40 and stop fluid flow. To open valve 5 the polarity of the electric potential applied to spaced electrodes 130 is reversed. It should be noted that because of the resistance of dielectric medium 120 to pressure driven flow, i.e., a pressure of several thousand psi can be required to force fluid through the dielectric medium, simply shutting the applied electric potential will generally not cause valve 5 to open. Further, because the hydraulic forces generated by the instant invention can be as great as 5000 psi or more this valve is capable of controlling high pressure lines. Moreover, because chamber 20 and inlet line 45 are filled with fluid the addition of only that amount of fluid necessary to cause displacement of flexible member 30 is required and thus, the response time of the valve can be very rapid. The response time of the valve can also be improved by minimizing the dimension between the proximal end of fluid inlet line 40 and flexible member 30.

Figure 2:
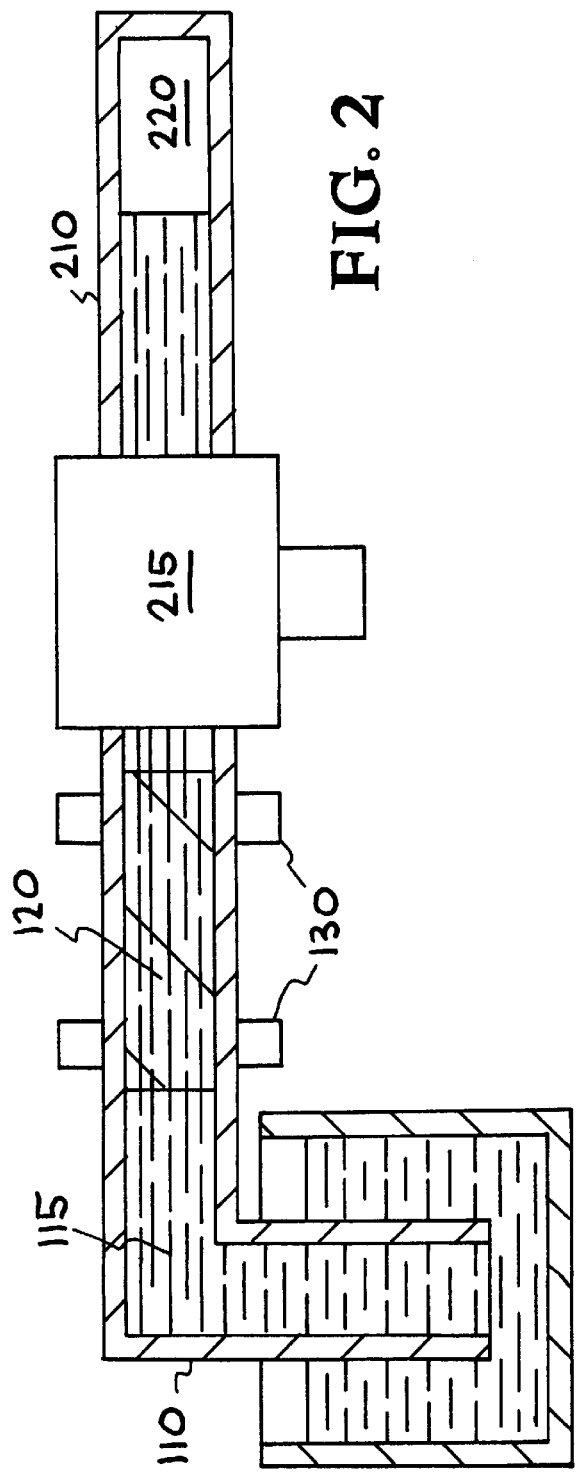
FIG. 2 illustrates a compressor embodiment.

The use of the present invention as a means for compressing a fluid, preferably a gas, within a flow channel can be illustrated by reference to FIG. 2. One open end of microchannel 110 containing porous dielectric material 120 is submerged in electrolyte 115. The opposite open end of microchannel 110 is connected one leg of "T" fitting 215. One end of capillary 210 is connected to the opposite leg of fitting 215 and the other end of capillary 210 can be sealed shut. An electric potential is applied by a power supply (not shown) between spaced electrodes 130 in contact with electrolyte 115. Electro-osmotic forces generated in microchannel 110 cause electrolyte 115 to advance by electro-osmotic pumping into microchannel 110 and further into capillary 210. The advance of electrolyte 115 (pumping) is stopped when the pressure of fluid 220 constrained in the sealed end of capillary 210 is high enough to counterbalance the electro-osmotic force produced by the electric potential applied to spaced electrodes 130, i.e., when the pressure of fluid 220 equals the electro-osmotic force generated by the applied electric potential. Shutting off or reducing the applied electric potential causes electrolyte 115 to retreat until the forces are once again balanced.

Figure 3:
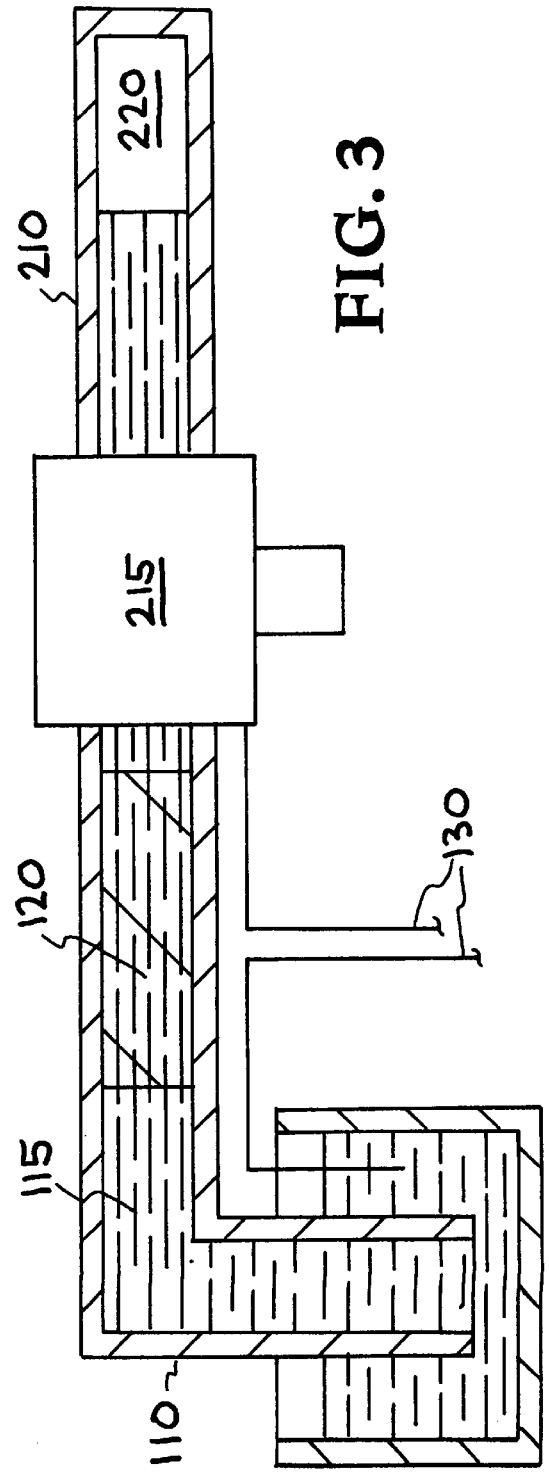
FIG. 3 shows an application of the present invention to compressing a gas.
Figure 4:
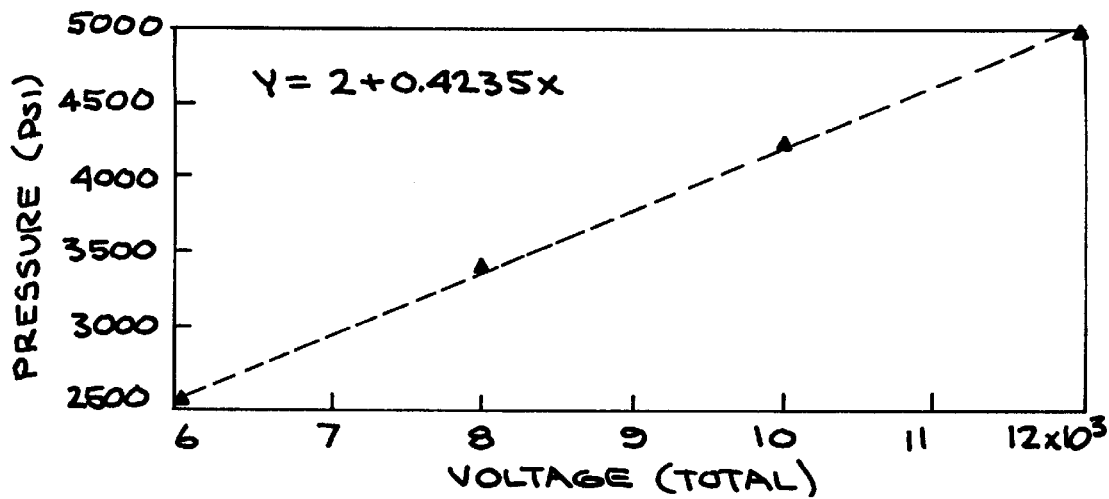
FIG. 4 illustrates the relationship between applied electric potential and pressure generated by the instant invention.

By way of example, a 15 cm long fused silica capillary 110 (as shown in FIG. 3) having a 75 μm inside diameter was packed with silica spheres 120 having a diameter of about 3 μm. The packed column was wetted with electrolyte 115, here water buffered with a trisodium phosphate buffer to a pH of 8.6. One end of the packed capillary 110 was then submerged in electrolyte 115 that also contained one electrode 130. The opposite end of packed capillary 110 was sealed into one leg of HPLC fitting 215 that served as another electrode 130. One end of an open fused silica capillary 210 was sealed into the other leg of HPLC fitting 215. Power was supplied to electrodes 130 to cause electrolyte 115 to be electro-osmotically pumped through packed column 110 and into open capillary 210. Having wetted a portion of the open capillary the opposite end of open capillary 210 was sealed shut. Power was again supplied to electrodes 130 until sufficient pressure was reached to counterbalance the electro-osmotic pumping force. For an applied field of about 300 V/cm a pressure in excess of 2500 psi was observed in the sealed end of capillary 210.

The pressure generated in this system is proportional to the electric potential and scales linearly with the length of the capillary, limited only by power dissipation or dielectric breakdown. In this context, it should be noted that in the presence of an applied field there will be ohmic heating of the microchannel and its contents and that this ohmic heating will have a substantially radial profile. The combination of a relatively high thermal conductivity aqueous electrolyte and the small physical dimensions involved suggest that there will be only a small radial temperature gradient as a result of this heating. It is straight forward to efficiently remove the heat generated in a microchannel, which can be a fused capillary, using forced air or immersion in a heat transfer liquid.

In summary, the present novel invention is useful generally in any application where manipulation of fluids in microchannels, in general, and capillary channels, in particular, is required, particularly in such applications as remote actuation of valves and other components or where a compressed fluid can be used to drive a fluid charge at high pressure on demand through the action of a valve.

It will be understood that the above described arrangements of apparatus and the methods therefrom are merely illustrative of applications of the principles of this invention and many other embodiments and modifications may be made without departing from the spirit and scope of the invention as defined in the claims.

Sequence Listing

Not Applicable.

We claim:

1. A valve for the manipulation of a fluid, comprising:

a) an electro-osmotic pump capable of exerting a hydraulic force greater than 10 psi, comprising;
  i) a microchannel having a fluid inlet and outlet and a porous dielectric material disposed in said microchannel;
  ii) an electrolyte contained within said microchannel;

iii) spaced electrodes in communication with said electrolyte; and
iv) means for applying an electric potential to said spaced electrodes;
b) a housing, including;
  i) a first chamber having at least one fluid inlet and at least one fluid outlet sealingly connected thereto;
  ii) a second chamber containing a fluid and adapted to receive the output from the electro-osmotic pump connected thereto; and
  iii) a flexible member sealingly separating said first and second chambers and adapted to move in response to the hydraulic force generated by the electro-osmotic pump to close or open the fluid inlet.

2. The valve of claim 1, wherein said means applies an electric potential that varies in time.

3. The valve of claim 1, wherein the direction of application of the hydraulic force is determined by the polarity of the applied electric potential.

* * * * *